(12) United States Patent
Cole

(10) Patent No.: US 10,994,084 B2
(45) Date of Patent: May 4, 2021

(54) SUBSTANCE INHALATION SYSTEM AND METHOD

(71) Applicant: Maury D. Cole, Spring Valley, CA (US)

(72) Inventor: Maury D. Cole, Spring Valley, CA (US)

(*) Notice: Subject to any disclaimer, the term of this patent is extended or adjusted under 35 U.S.C. 154(b) by 394 days.

(21) Appl. No.: 15/954,400

(22) Filed: Apr. 16, 2018

(65) Prior Publication Data
US 2018/0228990 A1     Aug. 16, 2018

Related U.S. Application Data

(63) Continuation-in-part of application No. 14/788,603, filed on Jun. 30, 2015, now Pat. No. 9,943,388.

(51) Int. Cl.
*A61M 15/00*     (2006.01)
*A61M 16/10*     (2006.01)
(Continued)

(52) U.S. Cl.
CPC ....... *A61M 15/0086* (2013.01); *A01K 1/0005* (2013.01); *A01K 1/031* (2013.01); *A01K 29/005* (2013.01); *A61M 15/0066* (2014.02); *A61M 16/0627* (2014.02); *A61M 16/1075* (2013.01); *A61M 16/14* (2013.01); *A61B 5/00* (2013.01); *A61M 11/042* (2014.02); *A61M 15/0003* (2014.02); *A61M 15/0021* (2014.02); *A61M 16/0009* (2014.02); *A61M 16/0063* (2014.02); *A61M 16/0093* (2014.02); *A61M 16/022* (2017.08); *A61M 2202/0007* (2013.01); *A61M 2202/0484* (2013.01); *A61M 2205/13* (2013.01); *A61M 2205/3569* (2013.01);
(Continued)

(58) Field of Classification Search
CPC ........ A61M 15/0086; A61D 7/00; A61D 7/04
See application file for complete search history.

(56) References Cited

U.S. PATENT DOCUMENTS 2,111,654 A    3/1938   Wires
2,141,794 A   12/1938   King
(Continued)

OTHER PUBLICATIONS

International Search Report and Written Opinion dated Jul. 1, 2019 for related International Application No. PCT/US2019/027095, in 15 pages.

*Primary Examiner* — LaToya M Louis
(74) *Attorney, Agent, or Firm* — Procopio, Cory, Hargreaves & Savitch LLP; Lisel M. Ferguson

(57) ABSTRACT

A stand-alone chamber or multi-chamber inhalation system has at least two alternative vaporized test liquid supply systems for passive or self-administered delivery of vaporized test fluid and air to one or more test chambers, which can be passive or restraint chambers, based on operator selection of delivery on and off times in a passive mode or actuation of an actuator in the chamber by a test animal in a self-administered mode. In one case, a multiple inhalation chamber system has two or more separate test fluid delivery systems and provides options for selective passive uniform drug delivery to multiple chambers or selective delivery of two or more different drugs to different groups of chambers from different delivery systems so that two different drugs or different concentrations of delivered drugs can be tested simultaneously.

9 Claims, 11 Drawing Sheets

(51) Int. Cl.
*A01K 1/00* (2006.01)
*A01K 29/00* (2006.01)
*A61M 16/06* (2006.01)
*A61M 16/14* (2006.01)
*A01K 1/03* (2006.01)
*A61M 16/00* (2006.01)
*A61B 5/00* (2006.01)
*A61M 11/04* (2006.01)

(52) U.S. Cl.
CPC . *A61M 2205/3592* (2013.01); *A61M 2205/50* (2013.01); *A61M 2205/84* (2013.01); *A61M 2230/43* (2013.01); *A61M 2250/00* (2013.01)

(56) References Cited

U.S. PATENT DOCUMENTS

| | | |
|---|---|---|
| 3,367,308 A | 2/1968 | Quattrone et al. |
| 3,464,388 A | 9/1969 | Stout |
| 3,537,428 A | 11/1970 | Montgomery |
| 3,838,687 A | 10/1974 | Mosher |
| 4,348,985 A | 9/1982 | Leong |
| 4,520,808 A | 6/1985 | Labauve |
| 4,526,133 A | 7/1985 | Lomaglio |
| 4,593,650 A | 6/1986 | Lattuada |
| 4,690,100 A | 9/1987 | Thomas |
| 4,699,088 A | 10/1987 | Murray et al. |
| 4,781,146 A | 11/1988 | Spengler |
| 4,787,382 A | 11/1988 | Pekovic |
| 4,941,431 A | 7/1990 | Anderson et al. |
| 5,379,777 A | 1/1995 | Lomask |
| 5,400,744 A | 3/1995 | Coiro et al. |
| 6,158,434 A | 12/2000 | Lugtigheid et al. |
| 6,352,076 B1 | 3/2002 | French |
| 6,776,158 B1 | 8/2004 | Anderson et al. |
| 7,252,050 B2 * | 8/2007 | Cole .................... A61M 16/10 119/416 |
| 7,527,021 B2 | 5/2009 | Mead et al. |
| 8,006,692 B2 | 8/2011 | Smith et al. |
| 2003/0062042 A1 | 4/2003 | Wensley et al. |
| 2005/0051165 A1 | 3/2005 | Cole |
| 2009/0211534 A1 * | 8/2009 | Schenkel ................ A61D 7/04 119/420 |
| 2010/0175629 A1 | 7/2010 | Garmon |
| 2010/0175695 A1 | 7/2010 | Jamison |
| 2016/0287366 A1 | 10/2016 | Scott |
| 2017/0000082 A1 | 1/2017 | Cole |

* cited by examiner

SUBSTANCE INHALATION SYSTEM AND METHOD

CROSS-REFERENCE TO RELATED APPLICATIONS

This application is a continuation-in-part of non-provisional U.S. patent application Ser. No. 14/788,603, filed on Jun. 30, 2015, the contents of which are incorporated herein by reference in their entirety.

BACKGROUND OF THE INVENTION

Field of the Invention

This invention pertains generally to substance abuse research systems, and more particularly to substance inhalation systems and methods for test animals.

Description of Related Art

The destructive effects of alcohol and drugs such as THC (tetrahydrocannabinol), cocaine and other stimulants are vast and well known and have led to the creation of the National Institute on Drug Abuse (NIH) and National Institute of Alcohol and Alcohol Abuse (NIAAA). Over the years, investigators funded by NIH and NIAAA have developed several systems for the delivery of drugs and alcohol which include presenting the drug as a liquid diet; injecting alcohol via gastric, intraperitoneal or intravenous routes; and by exposing test subjects, e.g., rodents, to drug and alcohol vapors. Each method has advantages and drawbacks that are abundantly discussed in the available literature. However, one significant problem that has consistently plagued research is the difficulty in reaching predictable blood levels (BLs) of drug and alcohol and, if desired, maintain them within given values. Injections of a specific concentration of drugs or alcohol can be used but this procedure is very stressful unless the animals are equipped with indwelling permanent cannulae. This requires skillful surgical training. Gavage via the forceful placement of a special tube into the esophagus can be done but is also very stressful, particularly if it is used repeatedly. Also both methods (injections and gavage) induce rapid peak BLs followed by the disappearance of drugs and/or alcohol from the circulation. They cannot be used to maintain constant BLs over time. Feeding drugs or alcohol in the diet presents the advantage of voluntary drug intake but does not provide the investigator with significant control over the amount of drugs or alcohol consumed, and consequently BLs are not consistent.

All of these problems have been critical barriers in drug and alcohol research. For this reason, many investigators have turned to delivery of drugs and alcohol through vapors. This method, as presently used, allows preparation of animals with more predictable BLs than the diet. However, it has its own inherent technical obstacles. For example, presently available drug and alcohol vapor chambers systems are very large because they can contain up to fifteen test subject cages. These chambers typically require an entire dedicated room and are built "in house", which makes the data collected completely unique to each system. The results from such individualized systems cannot be compared to results from other research facilities or universities as they are all different systems. Therefore, it is often difficult to achieve reproducible results from chamber to chamber and from experiment to experiment. Another major obstacle with the current individual systems is that they are built to house many animals together. This requires the investigator to open the entire system to remove one animal, for example to check its BAL. This unavoidably destroys the balance in the system, which requires time to return to equilibrium. Additionally, the handling of the animal causes stress hormones such as corticosterone to be released, which can interfere with the outcome of the results. Finally, not only is the initial cost of building these systems very high, the expense to run them is also high given that they require a full-time employee dedicated to their maintenance.

U.S. Pat. No. 7,252,050 of Cole describes a portable substance inhalation system which has separate inhalation chambers on shelves of a housing supported on a wheeled cart, and a single vapor delivery system mounted on the cart and connected to the inhalation chambers by delivery lines. This overcomes some of the limitations in prior drug and alcohol delivery systems for test purposes.

SUMMARY

Embodiments described herein provide for a stand-alone or table top inhalation chamber system which provides multiple drug delivery and testing options, and for a multiple inhalation chamber system which provides options for selective uniform drug delivery to multiple chambers from a single, passive drug delivery system, and for delivery of two or more different drugs to different groups of chambers from different drug delivery systems so that two different drugs or different concentrations of delivered drugs can be tested simultaneously. In one embodiment, the multiple chambers of the chamber system are also each associated with their own individual drug delivery system for selective individualized testing of one or more drugs in different individual chambers in the system via the individual drug delivery systems associated with the chambers. In some embodiments, options for different types of drug vapor delivery to the same chamber are provided, for example drug vapor delivery by a positive air pressure system or liquid bubbler system, or by a negative pressure or vacuum pressure system connected to the test chamber which creates suction, drawing inhalable drug or alcohol vapor through the inhalation test chamber for inhalation by a test animal (e-vape inhalation system similar to e-cigarettes). In either case, the system can be used as a passive form of administration with drug infused vapor delivered at operator determined time periods, or in a self-administration mode in which drug infused vapor is delivered for a selected time period when an animal engages a nose poke or similar actuator. The system can be attached to one or more animal test chambers which allow for whole body exposure or a nose exposure restraining chamber.

This system provides more flexibility for the researcher to perform different experiments or drug testing using one or more different drugs or other potentially harmful substances such as nicotine, alcohol, cocaine, THC and other stimulants, and using different drug vapor delivery systems, delivery concentrations, delivery times and the like. A controller is connected to various components such as heaters, pumps, mixing chambers, e-cigarette attachments, and flow meters of the system and stores accumulated test data.

In one embodiment, a table top inhalation chamber system can function as an e-vape system or bubbler system depending on how it is hooked up. In one embodiment, the inhalation system includes multiple chambers for holding test animals and one or more bubbler systems for delivery of test vapor to the chambers. A test vapor can be selectively and individually provided to each inhalation chamber attached to the system. Multiple chambers can be attached to each system. Additionally, the first inhalation chamber and the second inhalation chamber can be selectively removed from the substance inhalation system without test vapor leaking from either inhalation chambers. The multiple chambers can be either whole body exposure chambers or nose exposure restraint chambers. Most labs prefer whole body exposure because the rodent is unrestrained and not stressed. When researching the effects of drug exposure on a particular molecular mechanism in the brain, stress hormones (such as corticosterone, adrenaline) can alter that effect so it's important to reduce stress. Thus, the overwhelming majority of users prefer whole body exposure where the rodent can roam around the exposure chamber just as he would in his housing cage and not induce stress. However, some labs do want to conduct nose exposures which requires the animal to be restrained and the vapor delivered directly to its face.

In one embodiment, the multi-chamber system is portable and comprises a cart or housing having plural wheels. One or more large liquid bubblers or mixing chambers and associated air and liquid pumps, controllers, and gauges are mounted on top of the housing or cart. In one embodiment a test fluid reservoir and an air source are in fluid communication with the mixing flask or bubbler. Air from the air source is mixed with a test fluid from the test fluid reservoir within the mixing flask. Two or more bubblers may be provided so that different drugs or substances may be provided to different chambers simultaneously, or all chambers can be supplied with the same test vapor at the same rate over the selected test time period or periods.

In another embodiment an e-cigarette attachment device as described below can be attached to the substance inhalation chamber. This allows experiments to be conducted with commercial disposable e-cigarettes. These e-cigarettes have a sealed cartridge that is pre-filled with nicotine (or THC) e-liquid. The attachment device allows users to insert the mouthpiece of the disposable e-cigarette into the e-cig smoking attachment. The e-cigarette attachment device works with the controller of the system to provide "puffs" of the e-cigarette at user-defined intervals and lengths as programed into the controller.

Other features and advantages of various embodiments will become more readily apparent to those of ordinary skill in the art after reviewing the following detailed description and accompanying drawings.

BRIEF DESCRIPTION OF THE DRAWINGS

The details of various embodiments will be more fully understood by reference to the following drawings which are for illustrative purposes only.

DETAILED DESCRIPTION

Certain embodiments as disclosed herein provide for a stand-alone or table top inhalation chamber apparatus or system with a single chamber and for a multiple inhalation chamber system which provides options for selective uniform drug delivery to multiple chambers from a single, passive drug delivery system which provides multiple drug delivery and testing options to multiple animals simultaneously.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention.

Figure 1:
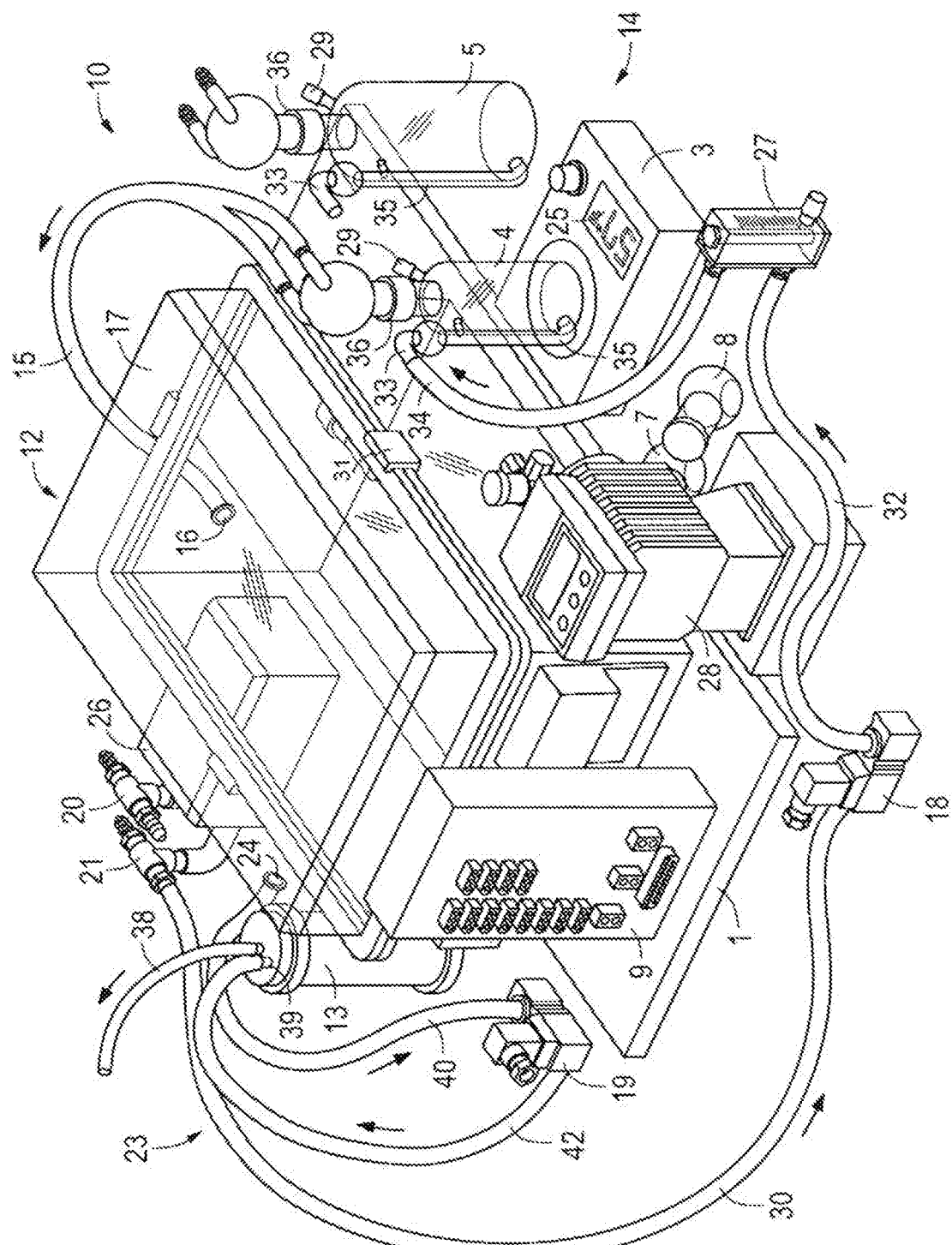
FIG. 1 is a perspective view of one embodiment of a stand-alone or table top substance inhalation system with one animal test chamber.

FIG. 1 illustrates a first embodiment of a standalone or table top inhalation apparatus 10. Apparatus 10 basically comprises a support platform or base 1, a test chamber 12 for holding an animal during substance testing, a liquid bubbler supply system 14 mounted adjacent chamber 12 for supplying metered quantities of a selected substance (e.g. alcohol, nicotine, cocaine, THC and other drugs or stimulants) to the interior of the chamber 12 via supply hose 15 connected to inlet 16 via a quick connect/disconnect between the end of hose 15 and inlet 16, a controller or control/connection box 9 which controls operation of the supply system, and an exhaust system 23 connected via outlet or exhaust hose 40 to chamber outlet 24 via quick connect/disconnect between the end of hose 40 and the chamber outlet 24. Chamber 12 is provided with a self-administration actuator comprising an active nose poke and inactive nose poke (not visible in FIG. 1), as known in the field. Chamber 12 has a lid 17 secured to the upper rim of the chamber by latches 31. A gasket is disposed between the lower rim of the lid and upper rim of the chamber to effectively seal the inhalation chamber when the latches are closed. The quick connect/disconnects are standard male/female quick disconnects, with the female having an attached shut off valve to prevent leakage after disconnection from the corresponding male connector.

The controller or computer system 9 in one example may be similar to the system described in U.S. Pat. No. 7,252, 050, the contents of which are incorporated herein by reference and may incorporate standard software as provided by Med Associates Inc. for controlling and monitoring components of the supply or delivery system and exhaust system, as well as for controlling timing and flow rates to the test chamber, collecting test data from test subjects, and detecting nose poke actuation in test chamber 12 when in the self-administration mode.

The bubbler system 14 comprises a first bubbler or mixing flask 4, a second, larger bubbler or mixing flask 5, a heater unit 3 incorporating a temperature controller with a temperature display window 25, a liter per minute gauge 27, an air compressor or vacuum pump 26, and a liquid pump 28 associated with test substance reservoirs or flasks 7, 8 which supplies test liquid to the bubblers 4, 5 via flask inlets 29. In one embodiment, liquid pump 28 is in fluid communication with a test fluid reservoir 7 or 8 and the mixing flask inlet 29. The pump is used to pump test fluid from the test fluid reservoir to the mixing flask.

Any suitable air compressor or vacuum pump 26 may be used, and in one embodiment the pump was a Hakko air compressor manufactured by Hakko of Laguna Hills, Calif. The air supply to air compressor 26 may be provided by ambient air as in the illustrated embodiment, or from an air tank, a valve from a laboratory air source, or the like.

Pump 26 has a pressurized air outlet T bar 21 and a vacuum outlet T bar 20. Pressurized air outlet 21 is connected to liter per minute gauge or flow meter 27 via outlet air hose 30, a first solenoid valve 18, and air supply hose 32. The controlled air outlet of liter per minute gauge 27 is connected via hose 34 either to an inlet 33 at the top of the smaller flask 4 seated on heater unit 3 as illustrated in FIG. 1, or to a similar inlet 33 at the top of larger flask 5 if a greater amount of test substance is to be supplied as a vapor to chamber 12, via a standard quick connect/disconnect fitting. As seen in FIG. 1, flasks 4, 5 each have an inlet air supply tube 35 extending from inlet 33 to the bottom of the respective flask. Flasks 4, 5 may be of any desired sizes and in one embodiment flask 4 is a 150 mL bubbler and flask 5 is a 250 mL bubbler. Each bubbler or mixing flask has an upper end outlet 36 which may be connected to test chamber inlet 16 via bubbled vapor supply hose 15.

In this embodiment, exhaust system 23 comprises an activated charcoal air scrubber 13 having a cleaned air outlet 38, first outlet or exhaust hose 40 connected between chamber outlet 24 and the inlet of a second three way solenoid valve 19, and a second outlet hose 42 connected between a first outlet of solenoid valve 19 and the inlet 39 of activated charcoal air scrubber 13. Cleaned air outlet 38 is suitably connected to the house exhaust system.

In operation, positive air pressure from the pump 26 passes through hose 30 and solenoid 18, and is regulated by liter per minute gauge 27 before entering the glass bubbler 4 or 5 (depending on which bubbler is connected to hose 34). Various sizes of bubbler or mixing flask may be provided with the apparatus for selective use, including more than two different size bubblers. The bubbler receives the liquid drug or other substance to be tested via liquid pump 28. The test fluid can be ethanol alcohol or any other liquid, solution, or the like to be tested, including drugs such as cocaine, THC, and other stimulants. Air enters the bottom of the bubbler via pipe 35 and mixes with the liquid to form bubbled drug or other substance-infused vapor which exits the bubbler via outlet 36. Bubbled, drug-infused vapor mixed with pressurized air supplied via liter per minute gauge or flow meter 27 enters the chamber via inlet 16 by positive air flow, and exits through outlet 24, passing through solenoid valve 19 and through charcoal scrubber 13, and leaves the area via hose exhaust 38, which may be connected to a standard lab exhaust.

The apparatus of FIG. 1 may be used for testing any substance in liquid form, such as alcohol or various drugs such as cocaine, THC, and other stimulants. Controller 9 controls supply of liquid to the bubbler chamber via liquid pump 28 and air supply amount via the liter per minute gauge 9, and operation of heater 3. Air flow through chamber 12 is continuous as long as an animal is in the chamber. The system of FIG. 1 can be used either for passive testing or for self-administration via nose poke, as desired by the user. If the user selects passive testing, the controller is programmed with desired on and off periods for supply of air and vapor mix to the chamber. During on periods, liquid is supplied to flask or bubbler 4 by liquid pump 28 via a hose (not illustrated) extending from the pump outlet to flask inlet 29, while air is supplied via hose 34, and the air and bubbled vapor is supplied via hose 15 to the chamber inlet and exhausted via chamber outlet 24. During off periods, liquid pump 28 is turned off so that air only is supplied to the chamber. When a self-administration test is selected, liquid pump 28 is turned on in response to a poke of the active nose poke by the animal in the chamber.

Figure 2:
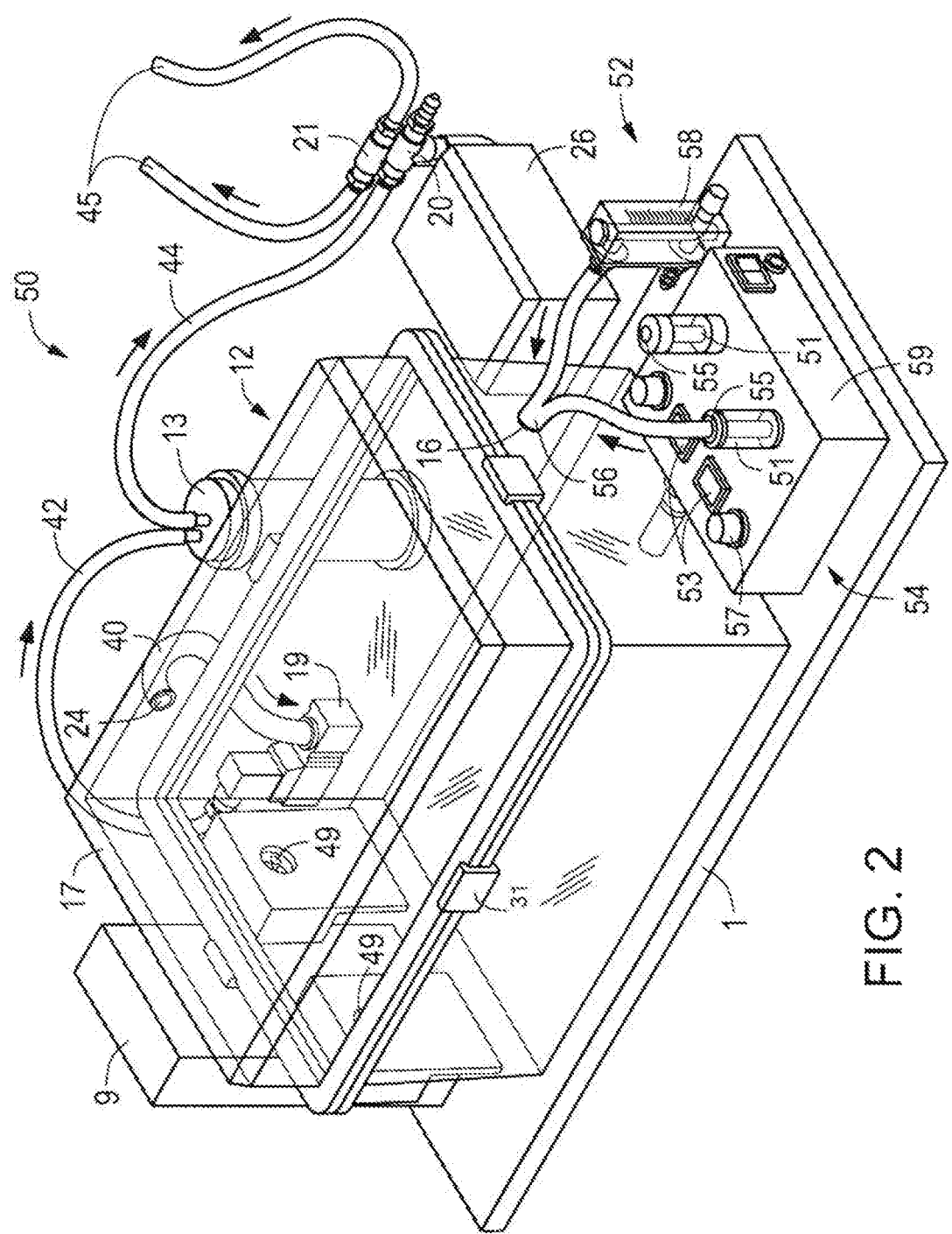
FIG. 2 is a perspective view of a second embodiment of a stand-alone substance inhalation system with one animal test chamber.

FIG. 2 illustrates a modified inhalation apparatus 50 according to a second embodiment, which has a different drug or test substance supply system 52 from the previous embodiment. However, several components of the apparatus or system 50 are identical to components of the previous embodiment, and like reference numbers are used for like parts as appropriate. FIG. 2 illustrates actuators or nose pokes 49 in chamber 12 which may be used for self-administration testing.

Supply system 52 of this embodiment includes a single or dual vape box or device 54 similar to vaporizers or nicotine delivery systems as used in e-cigarettes and the like. FIG. 2 illustrates a dual vape box which has dual cartridges or cylinders 51 containing an e-liquid including the substance or drug to be tested. The cartridges are removably mounted by threaded engagement with a respective atomizer outlet on top of housing 59 and communicate with an atomizer inside the housing. As in an e-cigarette, each replaceable cartridge contains a wick soaked in e-liquid containing the substance to be tested, such as nicotine or other drug, as well as a carrier such as propylene glycol (PG) or vegetable glycerol (VG) which creates an aerosolized vapor or smoke containing nicotine, in a similar manner to an e-cigarette. However, cartridges 51 are of more robust construction then e-cigarette cartridges. Cartridge 51 may be pre-filled with the liquid or the e-vape liquid containing the test substance or drug may be injected through the open top 55 of the cartridge. After filling, a quick connect/disconnect fitting 47 (see FIG. 3) is attached to the top 55 for releasable connection to a hose, such as one arm of Y-shaped hose 56 as seen in FIG. 2. In other embodiments, dual vape box 54 may be replaced by a single vape box with only one cartridge 51 and one set of associated controls. Cartridges 51 may be replaced as necessary. Housing 59 also contains the power supply for the atomizer heater and a vape box controller which is connected to control box 9 via wired or wireless connections. Also provided on top of housing 59 are dials 57 for controlling voltage for atomization to control the dose of atomized substance such as nicotine or other drugs, and display windows 53 which indicate current voltage.

As illustrated in FIG. 2, a selected one of the cartridge outlets 55 is connected to one side of a y-splitter hose 56 via quick connect/disconnect fitting 47 (illustrated in FIG. 3) to provide drug infused vapor via suction to the inlet 16 when outlet 24 is connected to a vacuum source, and a liter per minute gauge 58 is connected to the other side of y-splitter 56 to provide clean ambient air to inlet 16. When vape box 54 is turned off, ambient air only is supplied to chamber 12. The outlet of y-splitter 56 is connected to chamber inlet 16 via a male/female quick disconnect. In this embodiment as in the embodiment of FIG. 1, outlet hose 40 is connected from chamber outlet 24 to the inlet of solenoid valve 18, while a second outlet of the valve 18 is connected via hose 42 to the inlet of activated charcoal filter 13, and the outlet of filter 13 is connected via vacuum hose 44 to the vacuum outlet 20 of air compressor 26. The air outlet 21 of air compressor or vacuum pump 26 exhausts via outlet hoses 45, as indicated by the arrows, unless a bubbler system is also associated with test chamber 12, as illustrated in FIG. 3 and described in more detail below.

In the e-vape arrangement of FIG. 2, negative air pressure or vacuum pressure from pump 26 creates suction at chamber outlet 24. This allows clean air regulated by liter per minute gauge 58 to enter the chamber via air inlet 16 through one side of the Y-splitter 56. At the same time, drug containing vapor or smoke is also drawn into the chamber from the outlet 55 of vape box 54 through the other side of Y-splitter 56 by suction when the vape box is turned on. Air combined with drug infused vapor travels through the chamber where it is inhaled by a test animal, and exits the chamber via outlet 24. The mixture exiting the chamber passes through three way solenoid 19 and then travels through activated charcoal filter 13. Cleaned air exits filter 13 via hose 44 connected to the air compressor vacuum inlet, and is then supplied by the pump as clean positive air pressure at air outlet 21. Delivery system 52 is particularly suitable for nicotine testing, but may be used for testing of other drugs suitable for vacuum-induced vapor delivery. Controller 9 is connected to the vape box 54, pump 26, and liter per minute gauge via wires or wireless communication for adjustment of the concentration of vapor in the drug delivered via delivery system 52 and control of the delivery period. As noted above, when the vape box is turned off, the system continues to deliver air drawn into chamber 12 by suction at outlet 24 via the air delivery arm of Y-splitter 56.

The system of FIG. 2 allows for either self-administration or passive administration of drug or nicotine infused smoke to chamber 12. The operator may program controller 9 for either type of delivery. When self-administration is selected, the e-vape box is turned on for a predetermined time period each time the rat or other test animal pokes the active nose poke 49, and is then shut off so that pressurized air only is supplied to the chamber between test periods. When passive administration is selected, the operator can choose on and off periods via controller 9. The e-vape box 54 is then turned on and off for the selected periods for the duration of the test. When the e-vape box is on, the test chamber fills with drug infused smoke. Alternatively, the e-vape box may be turned off based on monitoring of animal test parameters such as drug levels in the blood.

Figure 3:
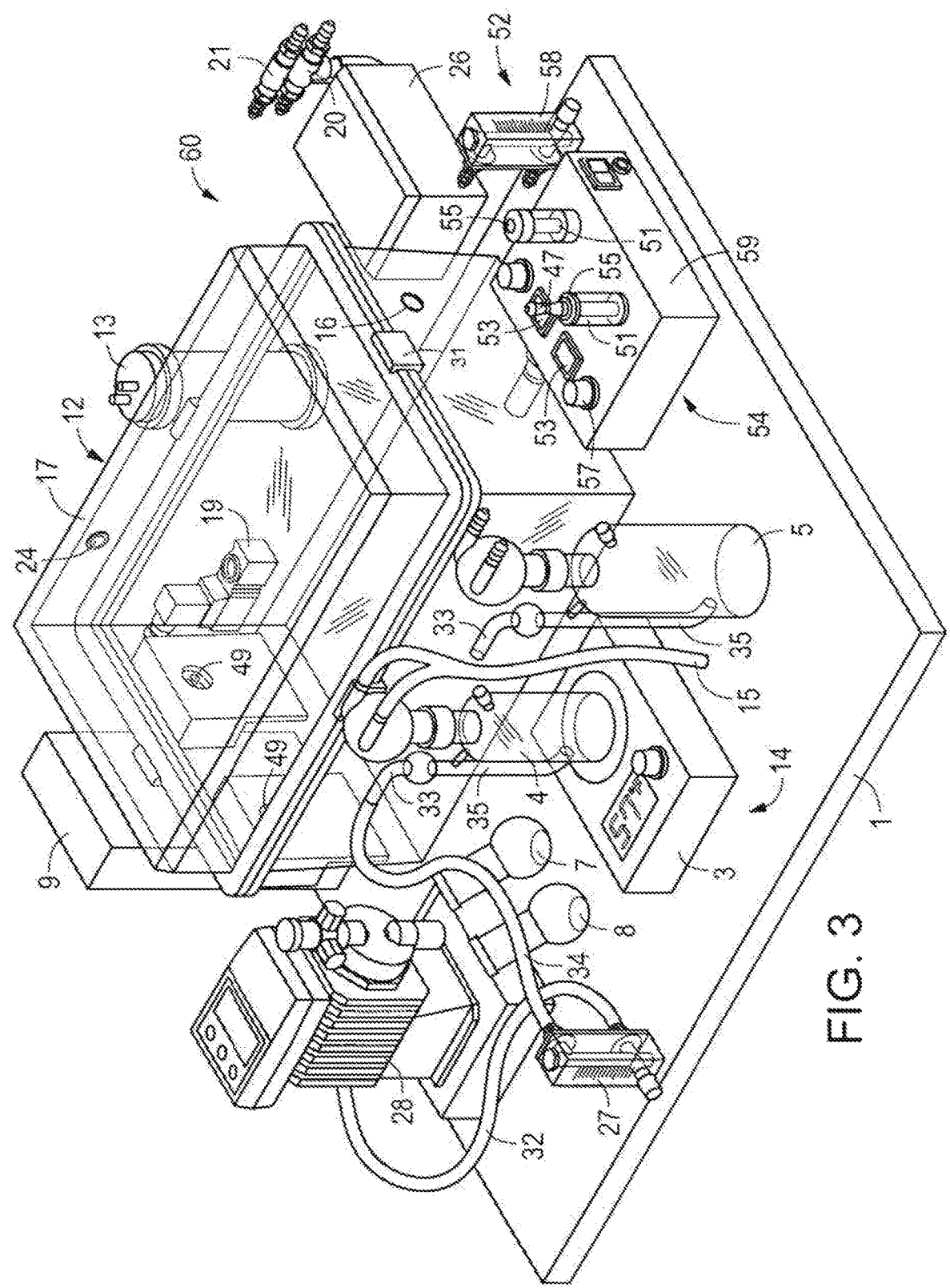
FIG. 3 is a perspective view of a third embodiment of a stand-alone, single chamber substance inhalation system with two different delivery options for passive or self-administration supply of different test vapors to the chamber.

FIG. 3 illustrates a third embodiment of a standalone or table top inhalation apparatus 60. This apparatus is a combination of the supply systems of FIGS. 1 and 2 and includes both the liquid bubbler supply system 14 of FIG. 1 and the vape box supply system 52 of FIG. 2, and like reference numbers are used for like parts. This provides more flexibility for the user to test different drugs using the same test chamber 12, such as alcohol, cocaine, THC or other stimulants using the bubbler system and nicotine or other drugs via the e-vape system. In FIG. 3, the bubbler supply system 14 and e-vape or vape box supply system 52 are supported around chamber 12 and utilize the same air compressor 26 as well as sharing other system components, as described in more detail below. Some hoses are omitted in FIG. 3 for clarity, and reference is made to FIGS. 1 and 2 for the hoses included with both systems.

Apparatus 60 is multi-functional and can be used to test a liquid drug using bubbler system 14 connected as illustrated in FIG. 1 (alcohol or other drugs in liquid form such as cocaine, THC and other stimulants) or a vape box or e-vape set up with vacuum using vape box 52 for testing nicotine and other drugs including those listed above, connected as illustrated in FIG. 2. Either system can be used in a passive mode using administration times selected by the operator, or in a self-administration mode using nose pokes 49 and the e-vape box system or bubbler system. By providing multiple alternative drug/test substance supply systems with the same test chamber, more flexibility is provided to the experimenter to test different ways of supplying test vapors to an animal before expanding to a multi-chamber system.

In FIG. 3, both the bubbler input hose 15 and the vape box input Y-splitter 56 are shown disconnected from chamber inlet 16, although in practice one or the other of the input hoses are connected to the inlet 16 and one of the outlet hoses is connected to outlet 24 at all times. When the system is not in use, any drug supply is turned off while the air supply hoses continue to supply air to the chamber, since the chamber is otherwise sealed. If the user wishes to use the bubbler system, they connect hose 15 to inlet 16 in FIG. 3 and outlet hose 40 (FIG. 1) to outlet 24, while air supply hose 30 is connected from pressurized air supply outlet T 21 of the compressor 26 to one of the inlets of the three way solenoid valve 18 to provide pressurized air to the bubbler flask via liter per minute gauge 27. If the user wishes to use the e-vape or vape box system, Y splitter hose 56 is connected to chamber inlet 16. Outlet hose 40 is still connected to outlet 24 of the vape box, but instead of cleaned air exhaust outlet 38, a vacuum hose 44 is connected from the vacuum outlet T 21 of air compressor 26 to the outlet of carbon filter or air scrubber 13, as is shown in FIG. 2, providing suction at chamber outlet port 24.

Figure 4:
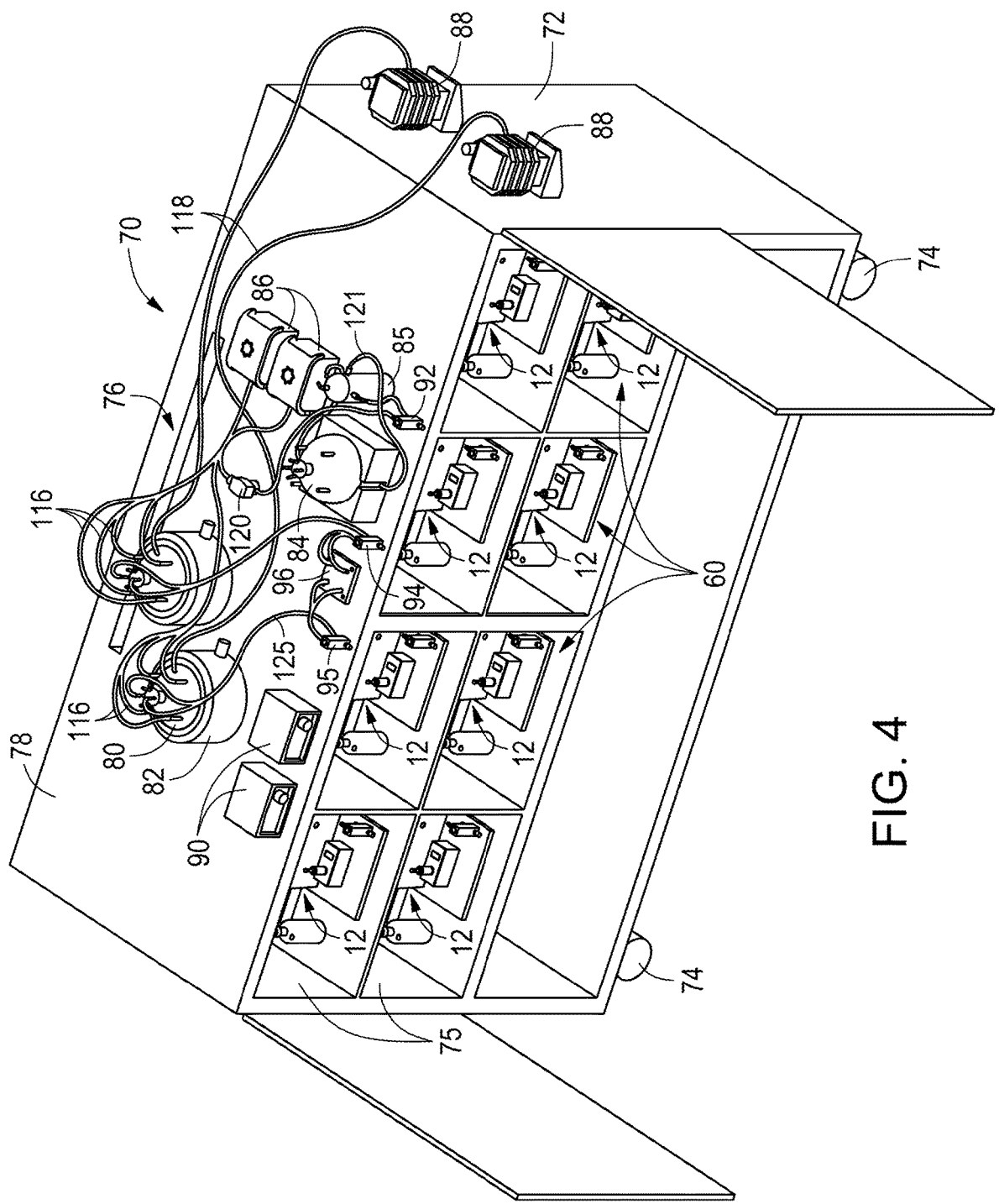
FIG. 4 is a front perspective view of one embodiment of a multi-chamber substance inhalation system.
Figure 5:
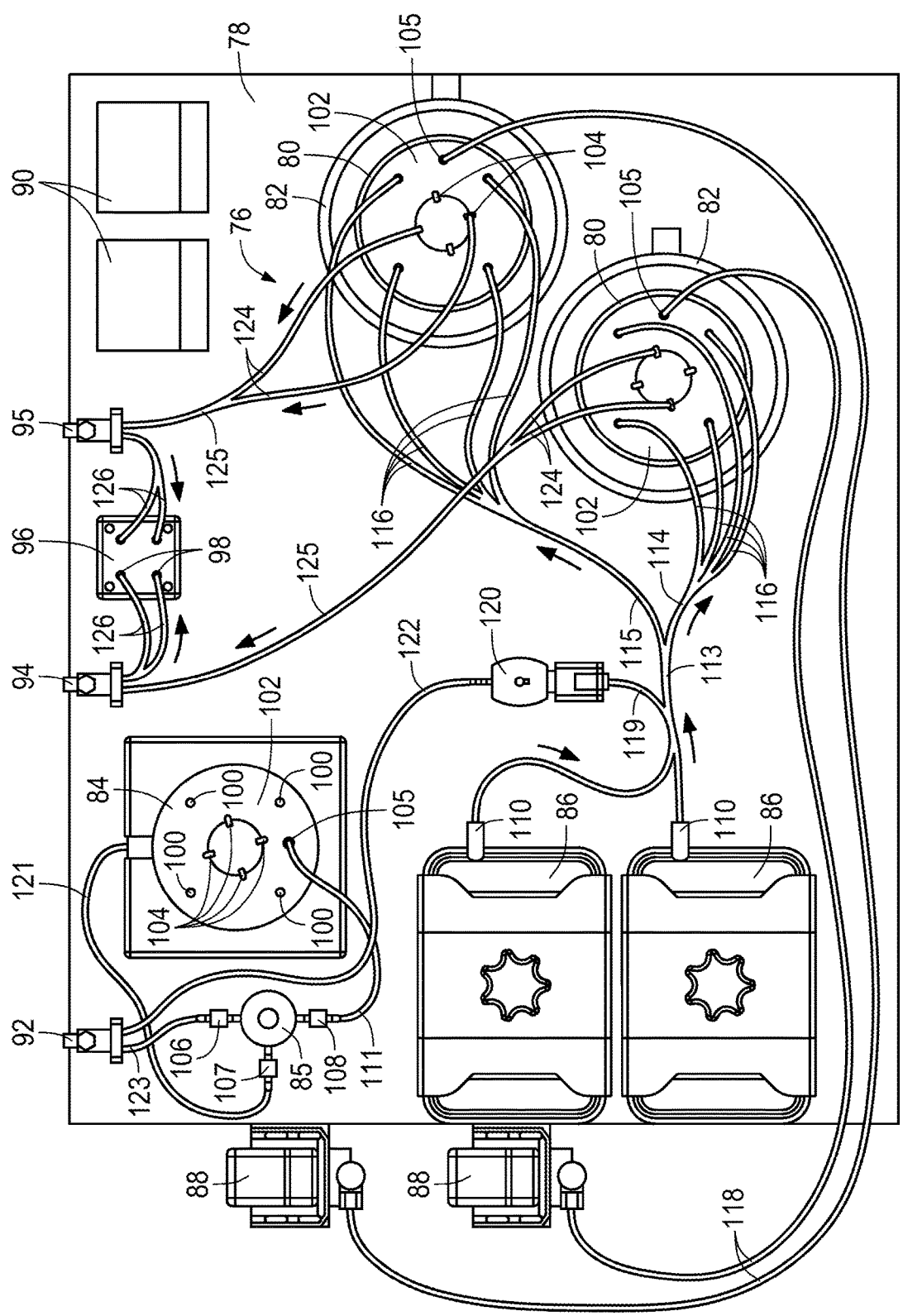
FIG. 5 is a top plan view of the test vapor supply system or apparatus for the multi-chamber substance inhalation system of FIG. 4.
Figure 6:
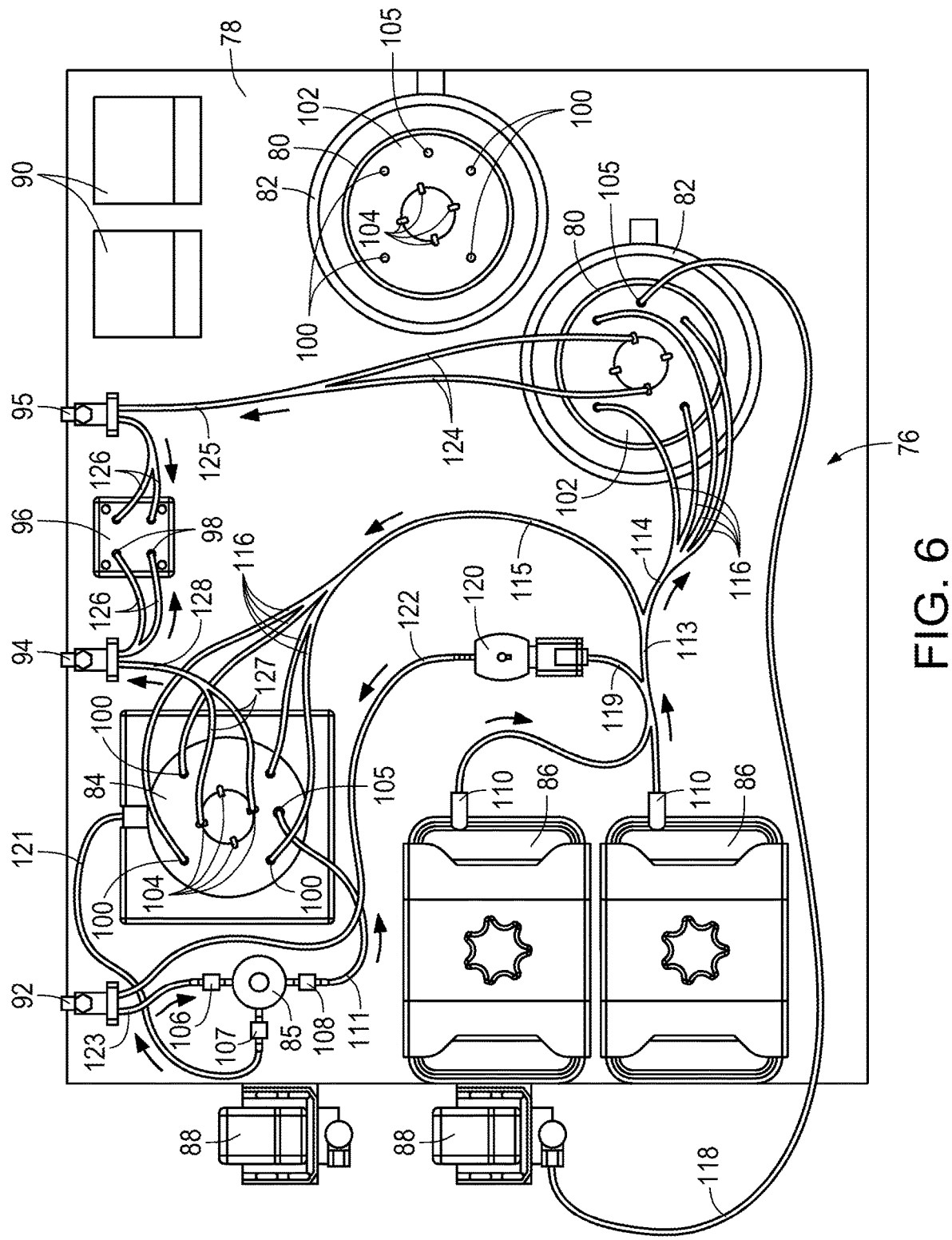
FIG. 6 is a top plan view of the supply system of FIG. 5 illustrating a different connection arrangement for drug supply to different sets of inhalation chambers.
Figure 7:
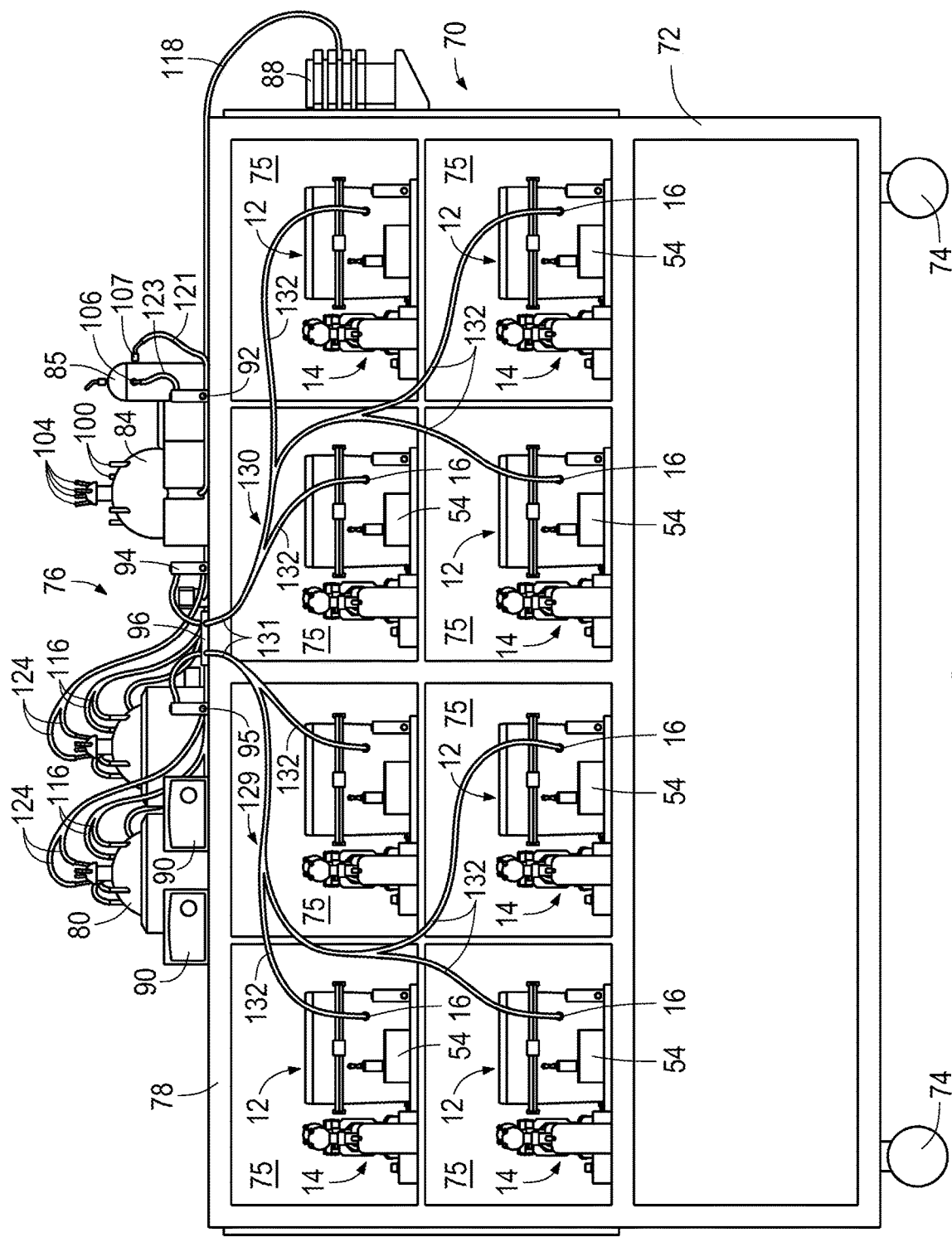
FIG. 7 is front elevation view of the multi-chamber substance inhalation system of FIGS. 4 to 6, illustrating hoses connecting the test vapor supply system to the chambers.

FIGS. 4 to 7 illustrate a multi-chamber inhalation system 70 according to another embodiment. The system 70 comprises a cabinet, housing or cart 72 with wheels 74, a plurality of test chambers 12 mounted in individual compartments 75 of the housing, and a passive test substance supply system 76 mounted on the top wall 78 of the housing, as best illustrated in FIGS. 4 and 7. In the illustrated embodiment, there are eight test chamber compartments 75, but a greater or lesser number of compartments are provided in other embodiments, for example a smaller housing may be provided with only four compartments and associated test chambers, depending on the requirements of the laboratory in which it is to be used. Also, the illustrated test chambers 12 are each associated with an individual bubbler system 14 and vape box system 52 so that they can alternatively be used individually in the manner described above in connection with inhalation system 60, as in FIG. 3. However, in other embodiments, individual test chambers 12 with no associated individual or stand-alone supply systems may be provided in each compartment 75 in place of the arrangement shown in FIGS. 4 and 7, or inhalation systems 10 or 50 of FIG. 1 or 2 may be provided instead of inhalation apparatus 60. Test chambers 12 of the multi-chamber system are identical to test chambers 12 of FIGS. 1 to 3, as are the associated individual bubbler systems 14 and vape box systems 52 if present, and like reference numbers are used for like parts as appropriate. Thus, it will be appreciated that the system can include inhalation chambers 12 with or without individual bubbler or vape systems, depending on a particular user's research needs.

The multi-chamber passive supply system 76 is configured to allow metered flow of one drug or substance to be tested or more than one substance to be supplied simultaneously under the same conditions to some or all of the test chambers 12, so that multiple test subjects are exposed to the same amount of drug or test substance for the same time period. System 76 is illustrated in more detail in FIGS. 5 and 6, which show two alternative possible arrangements of the system for supply of the same bubbled vapor or different bubbled vapors to the test chambers below. These figures show a smaller upper cabinet wall 78 which may be associated with a smaller, four chamber cabinet in another embodiment. However, the components of the passive bubbler system are the same for the larger, eight chamber cabinet of FIGS. 4 and 7, as best seen in FIG. 4, as well as for other size cabinets in other embodiments which may have more or less compartments.

System 76 basically comprises two identical heated glass flasks or mixing chambers 80 each mounted on a heater unit 82, a further glass flask or mixing chamber 84 which may be unheated, a liquid bubbler 85 associated with mixing chamber 84, and one or more air compressors 86. Two air compressors 86 are provided in the illustrated embodiment for redundancy purposes, in case one of the compressors fails. The system controller is programmed to monitor the compressors and switch from one compressor to the other automatically if failure of a compressor is detected. Two liquid pumps 88 are mounted on the side of cabinet 72 and include liquid drug or test substance reservoirs for supply to heated flasks 80 when in use. Heater controllers 90 are provided for control of heater units 82 based on outputs of temperature sensors in the flasks. Liter per minute gauges 92, 94, and 95 are mounted adjacent the front edge of wall 78, along with connecting manifold or plate 96 which has feed through openings 98 through wall 78 for connection of hoses to the various chambers, as described in more detail below. Mixing flasks 80 and 84 and may be of identical or different sizes. In one embodiment, each flask was a three liter glass flask, but different sizes may be provided in other embodiments. Mixing flasks 80 and 84 may be of the same general shape as mixing flasks 4 and 5 of FIGS. 1 and 3, or may have a generally spherical body as in U.S. Pat. No. 7,252,050 referenced above, and as illustrated in FIGS. 4 and 7. Four equally spaced bubbled liquid or vapor outlets 104 are provided in a ring at the top 102 of the flask. Four equally spaced pressurized air inlets 100 are provided at spaced intervals around an upper portion of each flask spaced outward from the top 102 of each flask or chamber. Each pressurized air inlet 100 is connected to a pipe or tube similar to pipe 35 of flask 4 or 5 of FIG. 1, but extending down inside the flask to the lower end of the flask 80, 84. The four pressurized air inlets with outlets at the lower end of the mixing flask provide for more uniform bubbling and mixing with liquid in the respective chamber. A separate liquid supply inlet 105 is provided in the upper wall of each flask. Liquid bubbler 85 is of smaller size than bubblers or flasks 80 and 84, and in one embodiment may be a 150 mL liquid bubbler. Bubbler 85 has a pressurized air inlet 106 and two outlets 107, 108 connected at spaced locations to an upper portion of bubbler 85, as seen in FIGS. 5 and 7.

Each air compressor 86 has a pressurized air outlet 110 connected via three way junction 113 to hoses 114, 115 and 119. Each hose 114, 115 has a four way split to four separate air supply hose portions 116 in an octopus like configuration, and hose portions 116 are connected to the respective four pressurized air inlets 100 of any two of the flasks 80, 84 via quick connect/disconnect fittings, at the selection of the user. Pressurized air supplied by either air compressor 86 to mixing flasks or bubblers via the air intake lines 114, 115, 119 can be ambient air. In the alternative, the air supply may be provided from an air tank, a valve from a laboratory air source, or the like.

All hose connections are via male/female quick disconnects as in the previous embodiments. FIG. 5 illustrates the four hose portions 116 of hoses 114, 115 connected to inlets 100 of the respective heated mixing flasks or bubblers 80, while FIG. 6 illustrates an alternative set up with one of the four way hoses 114 connected to inlets 100 of one chamber 80 and the other four way hose 115 having hose portions 116 connected to respective inlets 100 of mixing flask 84. FIG. 5 also illustrates the two liquid pumps 88 connected via supply hoses 118 to the respective liquid supply inlets 105 of flasks 80, while FIG. 6 illustrates only one of the liquid pumps 88 connected to the active flask 80.

The pressurized air outlets of air compressors 86 are also connected to the bubbler 85 via connecting hose portion 119 extending from junction 113 to solenoid valve 120. The outlet of solenoid valve 120 is connected via first pressurized air supply hose 122 to liter per minute gauge 92. The outlet of liter per minute gauge is connected by pressurized air supply hose 123 to the pressurized air inlet 106 of bubbler 85. Solenoid valve 120 is switched off in the set up or arrangement of FIG. 5 where bubbler 85 and mixing flask 84 are not in use, cutting off pressurized air supply to the bubbler 85. Bubbled liquid and air outlet 108 of bubbler 85 is connected to liquid supply inlet 105 at the top of bubbler 84 via hose 111, while bubbled liquid outlet 107 is connected via hose 121 to a second liquid supply inlet at the bottom of bubbler 85. One way valves in hoses 111 and 121 prevent backflow to bubbler 85.

In the set-up of FIG. 5, two bubbled vapor and air outlets 104 of each chamber or bubbler 80 are connected to separate hose sections 124 connected to liquid outlet hoses 125 via a Y connector. One outlet hose 125 is connected to an inlet of liter per minute gauge 94, while the other outlet hose 125 is connected to an inlet of liter per minute gauge 95. The branched outlet hoses 126 of liter per minute gauges 94, 95 are connected to respective openings in connecting manifold 96 for supply to respective test chambers, as described in more detail below.

In the alternative arrangement of FIG. 6, one of the heated flasks or bubblers 80 is not in use, and two inlet sections 127 of a Y-shaped outlet hose 128 are connected to bubbled vapor and air outlets 104 at the top of flask 84, while the outlet end of hose 128 is connected to the liter per minute gauge 94 in place of outlet hose 125 in FIG. 5.

FIG. 7 illustrates left and right hose connection assemblies 129, 130 from the openings in plate or manifold 96 to the inlets 16 of the respective test chambers 12 in housing 72. Each hose connection assembly has inlet portions 131 which are connected to outlet openings on respective right and left sides of manifold 96, and four outlet sections 132 from respective Y splits leading to respective chamber inlets 16. Although not illustrated in FIG. 7, the hose connection assemblies are arranged such that each hose path from a manifold opening or outlet 98 to a respective chamber inlet 12 is of approximately the same length. Sections that appear shorter in FIG. 7 include coiled hose portions for accommodating the different distances from manifold 96 to the respective chamber inlets while still ensuring an approximately equal liquid path to all chamber inlets. It will be understood that chamber outlets 24 are all connected via hoses to a common activated carbon air scrubber which in turn is connected to the hose exhaust in the configuration of FIG. 7. The chambers may also be connected to the same outlet carbon air scrubber when used for individual chamber tests, rather than having their own individual outlet scrubbers as in FIGS. 1 to 3.

Figure 8:
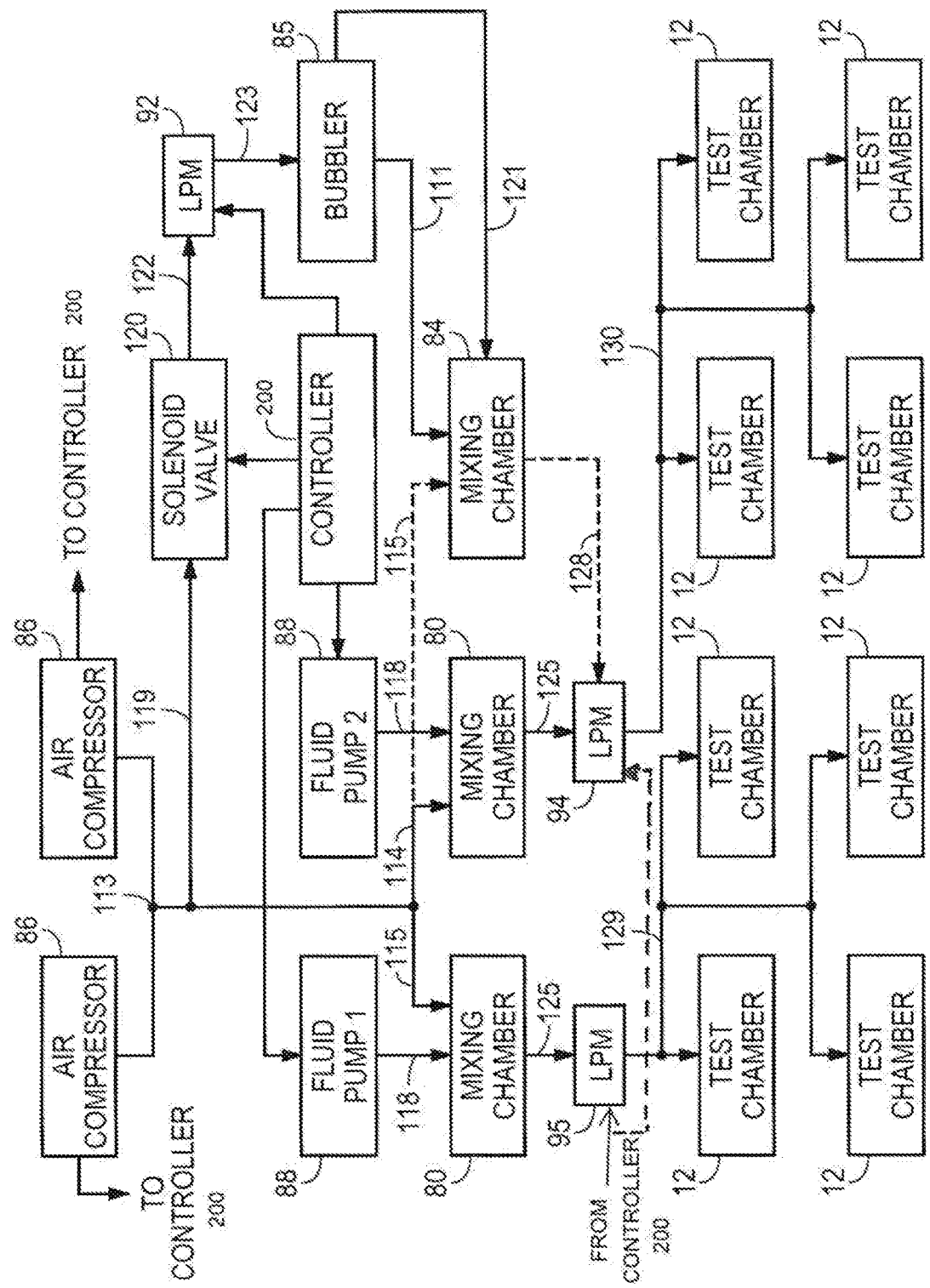
FIG. 8 is a block diagram illustrating one embodiment of a control system for controlling operation of the multi-chamber substance inhalation system.

FIG. 8 illustrates one embodiment of a control system for control of various components of the multi-chamber passive supply system of FIGS. 4 to 7. As illustrated, a controller 200 comprising one or more microprocessors is connected to fluid pumps 88, liter per minute gauges 92, 94 and 95, solenoid valve 120, and also monitors operation of air compressors 86 to provide an alarm if one or both compressors fail. Controller is also connected to the temperature controllers 90 (not shown in FIG. 8) to monitor and control temperature in the mixing chambers 80 by adjustment of heaters 82. The operator selects desired on and off periods for supply of drug or test fluid infused bubbled vapor to chambers 12, as well as desired flow rates, and also selects whether or not bubbler system 84, 85 is to be used. If this system is not in use, for example in the operation mode shown in FIG. 5, solenoid valve 120 is closed to stop pressurized air supply to bubbler 85 via LPM gauge 92, and thus no bubbled liquid is supplied to mixing chamber or flask 84.

When the system as illustrated in FIG. 5 is in use to supply the same test fluid or different test fluids to the chambers from mixing flasks 80, solenoid valve 120 is off and controller 200 is programmed to switch on both fluid pumps 88 for the selected inhalation period, and bubbled vapor and air is supplied to all test chambers simultaneously. At the end of the desired exposure or inhalation period, fluid pumps 88 are turned off while pressurized air continues to be supplied to the test chambers via hoses 114, 115 and via the test chambers and hose assemblies 129, 130 to the chambers. The cycle repeats at the start of the next ON period. When the system as illustrated in FIG. 6 is in use, the right hand fluid pump in FIG. 8 is turned off for the duration of the test. At the start of each inhalation test period, the left hand fluid pump 88 is turned on and solenoid valve 120 is opened, and different bubbled test vapors are supplied to the test chambers on the left and right in FIG. 7 via LPM 95 and LPM 94, respectively. At the end of the selected inhalation ON period, the left hand fluid pump 88 is turned off and the solenoid valve 120 is closed, shutting off test fluid supply to the active mixing flask 80 and to the mixing flask 84. At the same time, pressurized air is supplied to all chambers via path 114 and redirected path 115 through chamber 84, as shown in dotted line in FIG. 8.

The controller 200 may be housed inside the lower shelf of cabinet 72, for example, and is suitably connected to the various components of the system in a conventional manner. The controller may be programmed using standard software for controlling experiments using inhalation systems as provided by Med Associates, Inc., and is also configured to receive and store data such as test times, flow rates and vapor concentrations to the test chambers, and sensor outputs from the test chambers or animals in the chambers. Other test parameters collected by the microprocessor may be a blood drug level or alcohol level (BAL) parameter that can be monitored by taking blood samples from test subjects within the inhalation chambers. In the alternative, the BAL or drug level parameter can be a vapor measurement parameter, e.g., a humidity parameter, measured within each inhalation chamber. It can be appreciated that the manner in which a drug or alcohol blood level parameter relates to the test subjects can be determined empirically, i.e., by experimentation, for many test subjects of varying sizes and weights.

Figure 9:
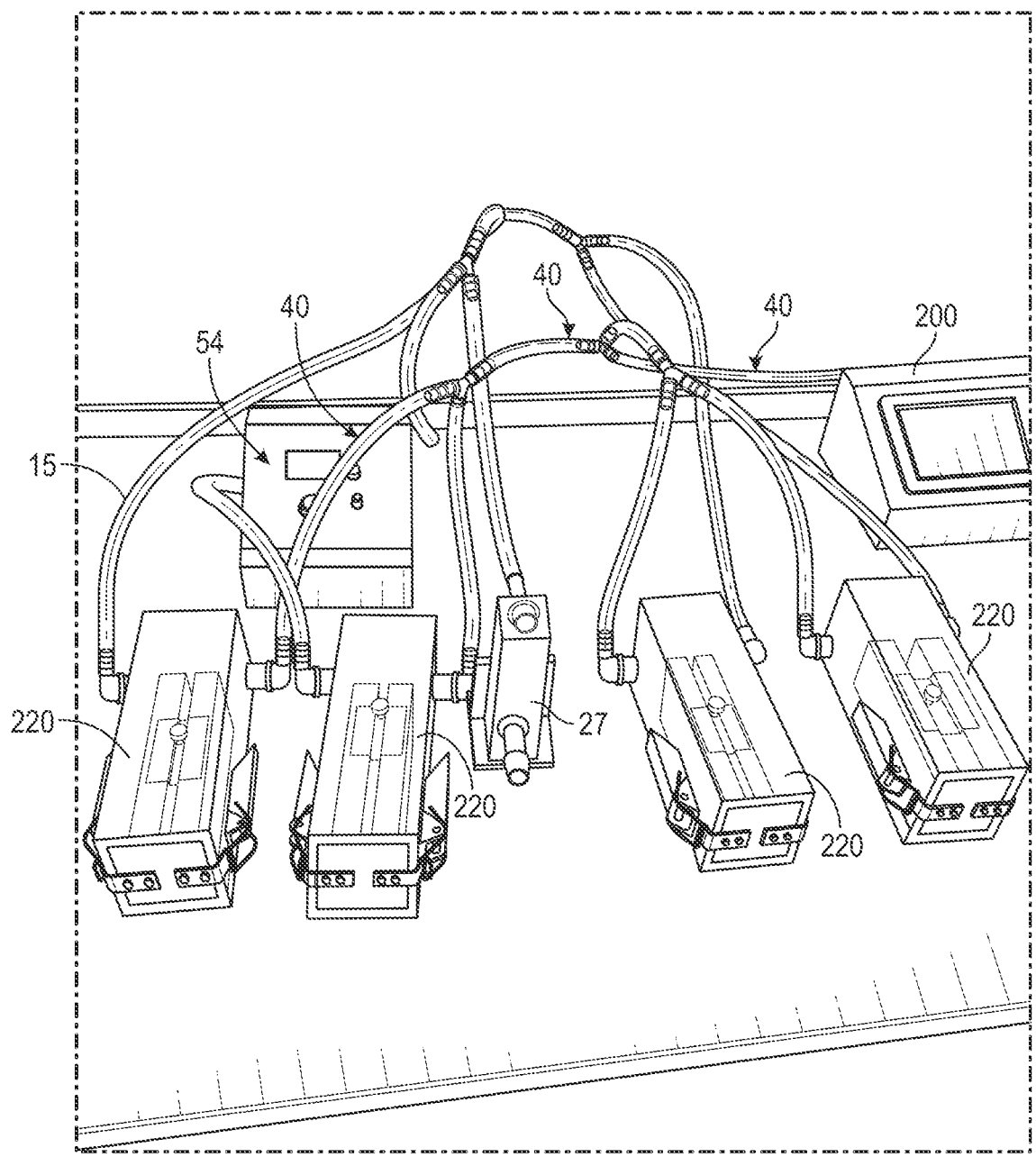
FIG. 9 is a perspective view of an embodiment of four restraint animal test chambers attached to a vape box and a controller of the a substance inhalation system.

FIG. 9 illustrates four animal restraint test chambers 220 attached to a vape box 54, a controller 200 and a flow meter 27 by way of tubing of the substance inhalation system. These restraint test chambers 220 can function with the systems as described in connection with FIGS. 1, 2, 3 and 4. Each of the four animal restraint test chambers 220 has supply hose 15 which leads to a vape box 54 and an exhaust hose 40 which leads to the vacuum pump FIG. 1 (26). Drug-infused vapor mixed with pressurized air supplied via liter per minute gauge or flow meter 27 enters the chamber via the supply hose 15 by positive air flow, and exits through outlet FIG. 1 (24) via the exhaust hose 40. The animal restraint test chambers 220 hold the animal secure so that it cannot move while the vapor is being blown into the chamber. There is a nose exposure attachment 234 in the chamber 220 which can be adjusted based on the size of the animal. The nose exposure attachment 234 has a hole in it where the test animal's nose can rest. The hole size in the nose exposure attachment 234 can be larger or smaller to accommodate various sizes of animals.

Figure 10:
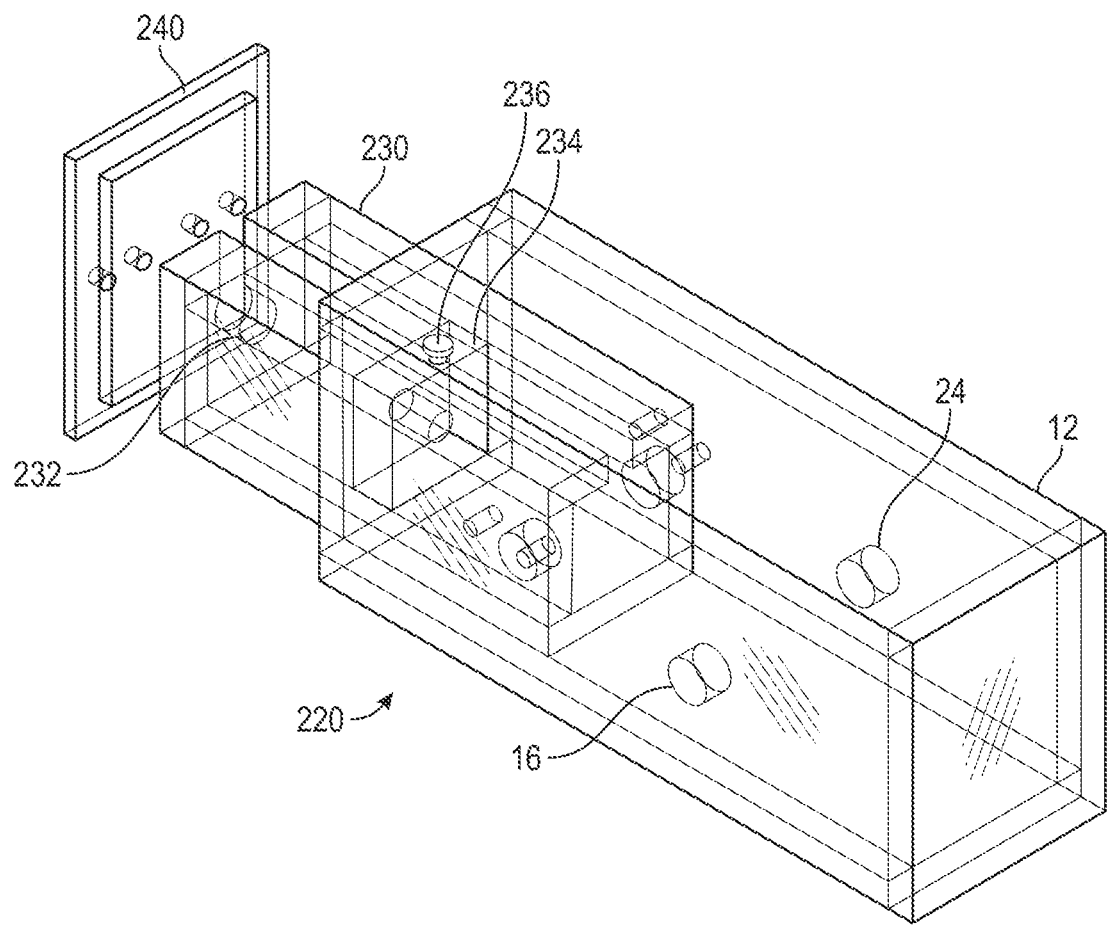
FIG. 10 is an exploded view of a single restraint animal test chamber of the substance inhalation system.

FIG. 10 illustrates an embodiment of an animal restraint test chamber 220 of the substance inhalation system. This is an exploded view which shows the regular signal test chamber 12 with a restraint housing 230 fitted inside. The restraint chamber slides inside the test chamber 12. An end plate 240 seals the chamber to make it air tight. The end plate 240 is connected to the test chamber 12 by way of clamps, or alternate attachment devices on either side. Once the end plate 240 is connected to the end of the test chamber 12 it is sealed and no vapor or gases can escape except through the chamber outlet 24 to which the exhaust hose 40 is connected The drug is pushed into the restraint test chamber 220 via the inlet 16 through the supply hose 15. The rodent is placed inside the restraint chamber 230. The back end of the rodent can be facing the end plate 240 so that the tail can extend through the hole 232 in the back end of the chamber. The exposure of the tail allows for blood samples to be easily drawn from the tail. The nose exposure attachment 234 is inside the restraint chamber 230 and can be adjusted backward or forward depending on the size of the rodent with the wing nut 236. The rodent's nose is placed into the hole in the nose exposure attachment 234 so that the vapor is blown directly toward the nose from the inlet 16 via a supply hose 15. Vapor is delivered directly to face and then vacuumed out to the exposure chamber and out through the outlet 24 as per normal whole body exposures. The nose exposure attachment 234 also serves as a restraint for performing the tail bleeds. Blood is always collected from the tail. Some labs purchase acrylic tail bleed restraining tubes for placing the rodent in with the tail out for collecting blood samples so this device is very helpful and serves a dual purpose.

Figure 11:
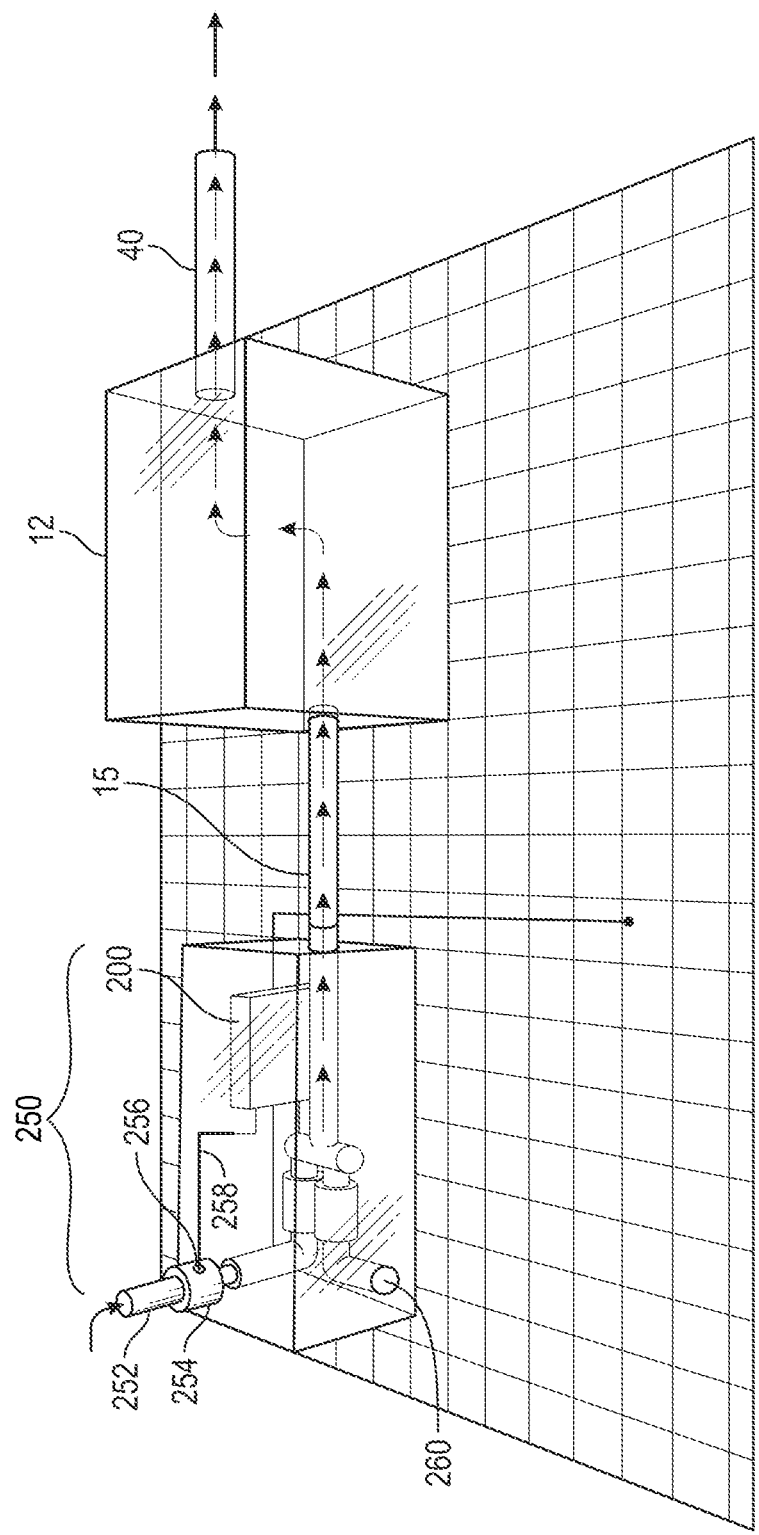
FIG. 11 is a perspective view of the commercial e-cigarette smoking attachment connected to an animal test chamber of the substance inhalation system.

FIG. 11 illustrates a of the commercial e-cigarette smoking attachment 250 connected to an animal test chamber of the inhalation apparatus FIG. 1(10). This attachment can be used with the inhalation apparatuses as described in FIGS. 1, 2, 3 and 4. It is an attachment so that commercial e-cigarettes can be used for testing lab animals in the system. The commercial e-cigarette smoking attachment 25 includes an inlet tube 262 which connects to the e-cigarette, a holder 254 including a control button or e-pin 254 into which the cigarette 252 fits. A wire or solenoid wire 258 is connected to the control button 254 at one end and the controller 200 at the other so that puffs of the cigarette can be administered to the test animal in the test chamber. Ambient air is mixed with the vapor from the e-cigarette. The ambient air is supplied through the inlet opening 260. The e-cigarette smoking attachment 250 is connected to one or more test chambers 12 via a supply hose 15 or tube. The rest of the inhalation apparatus runs as described in FIGS. 1, 2, 3, and 4.

In order to use the e-cigarette smoking attachment 250 the user takes e-cigarette and inserts it into the holder with the mouthpiece down so that when the control button 254 is triggered by the controller 200 the vapor goes straight through the supply hose 15 and directly into the test chamber 12. The vapor can mix with ambient air which is obtained from the outside through the inlet opening 260.

To use the e-cigarette smoking attachment 250 in connection with the inhalation apparatus FIGS. 1, 2, 3, and 4 (10) the vacuum pump FIG. 1(26) needs to be turned on very slowly until the flow meter or liter per minute gauge 92 reaches the desired air flow level. Next the solenoid 258 in line it up with the E-pin button 254. All of this needs to be done before putting a test animal into the chamber 12 so that the user can make sure the attachment is working properly. Next the power of the controller 200 needs to be turned to do a test run by programming the controller 200 for one to 10 sec hit primarily to make sure the button on the e-cigarette is not sticking and when the solenoid releases the button it goes back into place. The last step is to open the chamber 12 door put in the rodent and close the door to make sure it is air tight and your gauge 92 is back to the desired level before the experiment is commenced.

In each of the above embodiments, probed or unprobed test subjects can be placed in the inhalation chambers and monitored during the test fluid vapor inhalation process. Test chambers may be provided for use in the above embodiments in a range of different sizes for accommodating all types and sizes of lab animals, such as rats, mice, guinea pigs and the like. The embodiment of FIG. 3 allows different test substances to be supplied to one test chamber successively in a passive form of administration by the bubbler or e-vape system, or in a self-administration test using the nose pokes, rather than needing separate test chambers for different types of tests. The multi-chamber embodiment of FIGS. 4 to 7 provides flexibility in multiple chamber test set-ups, allowing the operator to test multiple animals more easily with simultaneous passive administration of the same substance or drug at the same concentration under the same conditions to all chambers, or to test two sets of animals simultaneously with different substances from different mixing flasks. Where the inhalation chambers are also provided with one or more individual passive vapor administration systems, as in any of FIGS. 1 to 3, even greater test flexibility is provided since some chambers may be used for individual passive tests or self-administration tests, while others are used for group tests. In the bubbler system, the microprocessor can control the vaporization of a test fluid within the mixing flasks 80 by altering the temperature, and can control flow from bubbler 85 to mixing chamber 84 by controlling air flow rate at LPM 92. Moreover, the microprocessor can control the flow of test vapors to the inhalation chambers by controlling the flow meters or liter per minute gauges 92, 94, 95 for multi-chamber administration and the liter per minute gauges 27 and 58 used for single chamber administration. The embodiments described above provide many options for testing various substances for potentially harmful effects, including alcohol, nicotine and drugs such as cocaine, THC, and other stimulants, as well as other substances for human use.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for".

What is claimed is:

1. A substance inhalation apparatus, comprising:
   at least one inhalation chamber having at least one inlet port and an outlet port, each port having a quick connect/disconnect fitting for releasable connection to a hose;
   a first supply system comprising a liquid bubbler supply system for supplying a first vaporized test liquid to the at least one inlet port;
   a second supply system comprising a vape box supply system for supplying a second vaporized test liquid to the at least one inlet port, the second vaporized test liquid different from the first vaporized test liquid;
   an exhaust system connected to the outlet port; and
   an actuator device,
   wherein the liquid bubbler supply system comprises a first bubbler, a test substance reservoir, a liquid pump that supplies a first test liquid to the first bubbler, and a heater associated with the first bubbler for heating liquid in the bubbler to a selected temperature, whereby the first test liquid supplied to the first bubbler is mixed with pressurized air to form the first vaporized test liquid;
   a first supply path between the liquid bubbler supply system and the at least one inlet port of the chamber which supplies the first vaporized test liquid to the at least one inlet port when the liquid pump is on and which supplies only pressurized air to the chamber when the liquid pump is off;
   wherein the vape box supply system comprises a vape box configured to vaporize a second test liquid to produce a second vaporized test liquid that is mixed with pressurized air and enters the inlet via a second supply path when the vape box is on and which supplies pressurized air only to the chamber when the vape box is off; and
   a controller connected to the actuator device and at least one of the liquid bubbler supply system and the vape box supply system, and the controller configured for user selection of a self-administration mode or passive mode, whereby the controller turns on the liquid pump or the vape box for a selected time period on activation of the actuator device by a test animal in the chamber when in a self-administration mode, and turns the liquid pump or the vape box on and off repeatedly for selected ON and OFF periods when in a passive mode.

2. The system of claim 1, wherein the inhalation chamber is a restraint chamber.

3. The system of claim 1, further comprising an e-cigarette attachment device configured to provide vapor from commercial e-cigarettes.

4. The system of claim 1, wherein the chamber outlet is connected to a vacuum source and the vape box comprises an e-vape unit comprising an atomizer and at least one vape cartridge having a first end connected to the atomizer and an outlet end, the vape cartridge containing a mixture of test substance and carrier liquid, and the second supply path having a first inlet end connected to the vape cartridge outlet and a second inlet end connected to a pressurized air supply, and an outlet communicating with the first inlet end and the second inlet end and connected to the at least one inlet port of the chamber, whereby the test substance infused vapor and air are drawn in to the chamber by the vacuum source when the e-vape unit is turned on and air only is drawn into the chamber when the e-vape unit is turned off.

5. The system of claim 4, wherein the second supply path is defined by a hose having separate inlets communicating separately with the vape cartridge outlet and the pressurized air supply and an outlet connected to the at least one inlet port of the chamber, whereby the test substance infused vapor and air are drawn in to the chamber by the vacuum source when the e-vape unit is turned on and air only is drawn into the chamber when the e-vape unit is turned off.

6. The system of claim 1, wherein the first vaporized test liquid is delivered through the at least one inlet port by positive air pressure.

7. The system of claim 1, wherein the actuator device is inside the inhalation chamber for test subject self-administration of at least one of the first and second vaporized test liquid.

8. The system of claim 1, wherein a vacuum source is connected to the outlet port and the first the second vaporized test liquids are drawn into the at least one inlet port by suction.

9. The system of claim 1, further comprising a liter per minute gauge connected to at least one of the first and second supply paths for controlling a flow rate of air and a flow rate of at least one of the first and second vaporized test liquids into the chamber.

* * * * *